(12) United States Patent
Mayer

(10) Patent No.: US 8,807,962 B2
(45) Date of Patent: Aug. 19, 2014

(54) MULTICELLULAR PUMP AND FLUID DELIVERY DEVICE

(75) Inventor: Felix Mayer, Stäfa (CH)

(73) Assignee: Sensirion AG, Stafa (SE)

( * ) Notice: Subject to any disclaimer, the term of this patent is extended or adjusted under 35 U.S.C. 154(b) by 1251 days.

(21) Appl. No.: 11/901,565

(22) Filed: Sep. 18, 2007

(65) Prior Publication Data

US 2008/0101971 A1 May 1, 2008

(30) Foreign Application Priority Data

Oct. 28, 2006 (EP) ..................................... 06022556

(51) Int. Cl.
*F04B 17/00* (2006.01)
*F04B 35/00* (2006.01)

(52) U.S. Cl.
USPC ..................... 417/321; 417/410.1; 417/413.1; 417/478; 91/5

(58) Field of Classification Search
USPC ........ 417/395, 413.1, 413.2, 413.3, 533, 321; 91/5
See application file for complete search history.

(56) References Cited

U.S. PATENT DOCUMENTS

| | | | |
|---|---|---|---|
| 3,606,592 A * | 9/1971 | Madurski et al. .......... | 417/413.1 |
| 4,889,962 A * | 12/1989 | Hagner ......................... | 174/250 |
| 4,938,742 A * | 7/1990 | Smits ............................. | 604/67 |
| 5,065,978 A * | 11/1991 | Albarda et al. ............... | 257/419 |
| 5,078,581 A * | 1/1992 | Blum et al. ................. | 417/413.3 |
| 5,129,794 A * | 7/1992 | Beatty ......................... | 417/413.1 |
| 5,171,132 A * | 12/1992 | Miyazaki et al. .......... | 417/413.1 |
| 5,284,179 A | 2/1994 | Shikida et al. | |
| 5,499,909 A * | 3/1996 | Yamada et al. ............... | 417/384 |
| 5,542,821 A | 8/1996 | Dugan | |
| 5,593,290 A | 1/1997 | Greisch et al. | |
| 5,839,467 A * | 11/1998 | Saaski et al. .................. | 137/501 |
| 5,891,097 A * | 4/1999 | Saito et al. ..................... | 604/141 |
| 6,059,546 A * | 5/2000 | Brenan et al. ................. | 417/534 |
| 6,074,178 A * | 6/2000 | Bishop et al. ................. | 417/322 |
| 6,106,245 A * | 8/2000 | Cabuz ........................... | 417/322 |
| 6,132,187 A * | 10/2000 | Ericson ........................ | 417/486 |
| 6,419,841 B1 * | 7/2002 | Snodgrass et al. ............. | 210/767 |
| 6,452,265 B1 * | 9/2002 | Furukawa et al. ............. | 257/723 |
| 6,481,984 B1 * | 11/2002 | Shinohara et al. .......... | 417/413.2 |
| 6,520,753 B1 * | 2/2003 | Grosjean et al. .............. | 417/379 |
| 6,550,324 B1 | 4/2003 | Mayer et al. | |
| 6,729,856 B2 | 5/2004 | Cabuz et al. | |

(Continued)

FOREIGN PATENT DOCUMENTS

| | | |
|---|---|---|
| EP | 0518524 | 12/1992 |
| WO | 0028215 | 5/2000 |

(Continued)

*Primary Examiner* — Devon Kramer
*Assistant Examiner* — Amene Bayou
(74) *Attorney, Agent, or Firm* — Cooper & Dunham LLP

(57) ABSTRACT

The pump is provided with a plurality of pumping chambers and electrically activatable valves. An elastic membrane is arranged in each pumping chamber and divides the same into a first and a second chamber section. Each valve is connected to the second chamber section of a pumping chamber. When a pressure drop is applied over the valve and the valve is activated (i.e. opened), the pressure in the second chamber section changes, which causes the membrane to move, which in turn leads to a change of the volumes of both chamber sections. This e.g. allows to pump well-defined amounts of fluid from the chamber sections to a drug dispensing device.

27 Claims, 3 Drawing Sheets

(56) References Cited

U.S. PATENT DOCUMENTS

| | | | |
|---|---|---|---|
| 6,767,190 B2 * | 7/2004 | Cabuz et al. | 417/53 |
| 6,869,275 B2 * | 3/2005 | Dante et al. | 417/413.2 |
| 6,921,253 B2 * | 7/2005 | Shuler et al. | 417/559 |
| 6,939,618 B2 * | 9/2005 | Rastegar | 428/543 |
| 7,040,338 B2 | 5/2006 | Unger et al. | |
| 7,104,767 B2 * | 9/2006 | Lee | 417/413.1 |
| 2004/0011977 A1 * | 1/2004 | Hower et al. | 251/11 |
| 2005/0074340 A1 * | 4/2005 | Xu et al. | 417/395 |
| 2006/0186085 A1 | 8/2006 | Fuertsch et al. | |

FOREIGN PATENT DOCUMENTS

| | | |
|---|---|---|
| WO | 0218783 | 3/2002 |
| WO | 02053290 | 7/2002 |
| WO | 03031822 | 4/2003 |

* cited by examiner

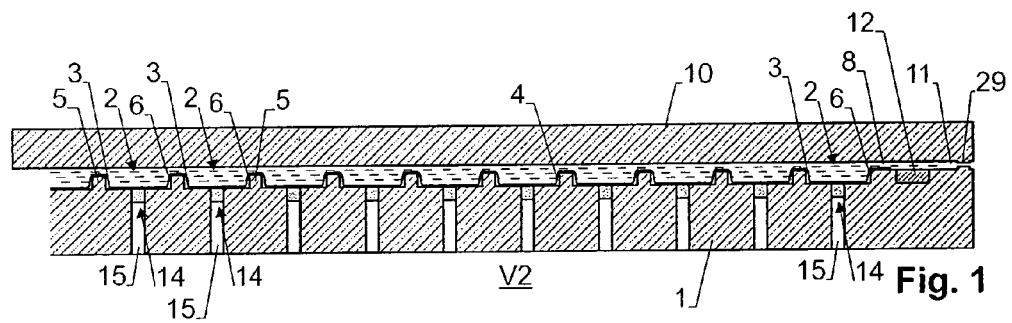
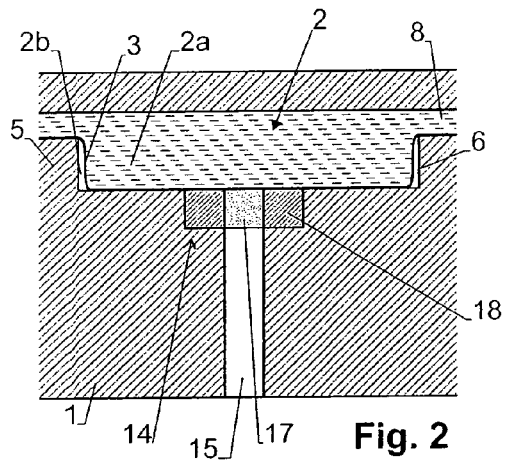
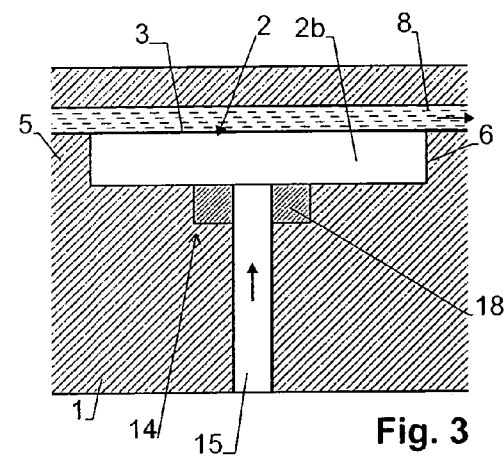
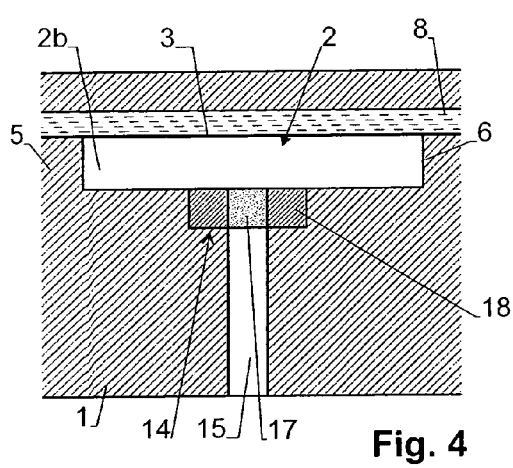
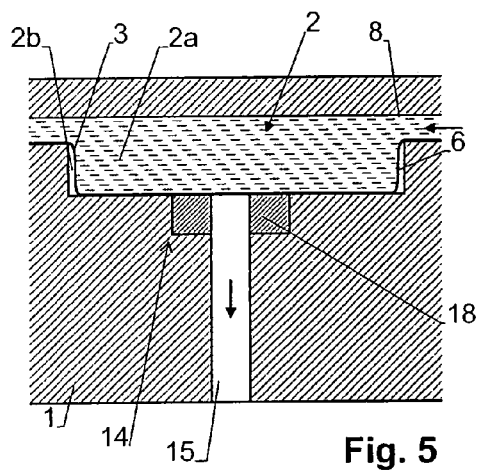
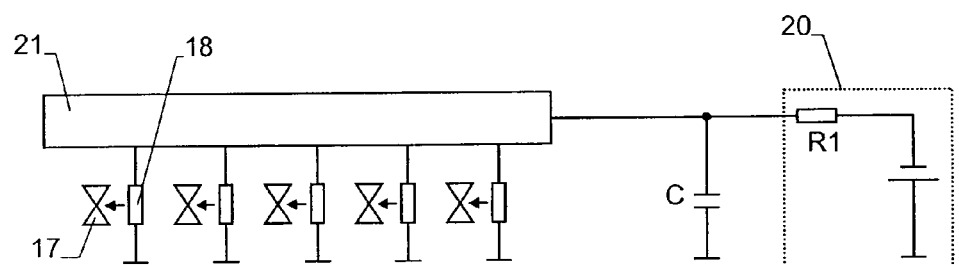

MULTICELLULAR PUMP AND FLUID DELIVERY DEVICE

CROSS REFERENCE TO RELATED APPLICATIONS

This application claims the priority of European patent application 06022556.2, filed Oct. 28, 2007, the disclosure of which is incorporated herein by reference in its entirety.

BACKGROUND OF THE INVENTION

The invention relates to a fluid delivery device, a multicellular pump and to a method for operating the same.

Multicellular pumps, i.e. pumps conveying a liquid by means of a plurality of individual cells, are able to convey small amounts of fluid in accurate manner, which makes them particularly attractive for various applications, e.g. in the fields of drug delivery, chemical analysis, or fuel delivery to fuel cells.

Designs suitable for microfabrication have e.g. been proposed in WO 00/28215 and use electrostatic forces for conveying the fluid.

U.S. Pat. No. 5,593,290 describes a delivery device where a fluid is delivered from an external reservoir by means of a peristaltic pump assembly comprising a plurality of chambers with membranes. The membranes are operated by pressure sources for conveying the liquid.

WO 03/031822 describes a pump with two chambers arranged in series and a flexible membrane arranged in each chamber. The membranes are alternatingly actuated for conveying the liquid.

BRIEF SUMMARY OF THE INVENTION

Many applications, e.g. for portable equipment, require pumps or fluid delivery devices having low power consumption. Hence, the problem to be solved by the present invention is to provide a multicellular pump or device that is particularly suited for low power applications.

Hence, it is a general object of the invention to provide a pump and device of the type mentioned above suited for low power applications.

A first aspect of the invention relates to a fluid delivery device that has a reservoir for holding the target fluid to be delivered, a plurality of pumping chambers and a deformable membrane arranged in each pumping chamber. The membranes divide each pumping chamber into a first and a second chamber section. Furthermore, the device comprises a plurality of elastic energy storage means, each of which is held by an electrically releasable retaining mechanism in an elastically deformed state and is releasable, by an electric signal fed to the retaining mechanism, to relax at least partially from the deformed state to a relaxed state. By releasing the energy storage means the membrane is moved from a first position to a second position thereby decreasing the volume of the first chamber section and increasing the volume of said second chamber section. The reservoir is formed by the first chambers, i.e. no external reservoir or target fluid input is required.

This type of device can be operated using a very small amount of electric energy because the energy for conveying the liquid is stored in the elastic energy storage means.

Advantageously, the elastic energy storage means are formed by the membranes in the chambers, for which purpose the membranes should be elastic.

The retaining mechanism can e.g. be formed by an electrically activatable valve or an electrically releasable attachment, such as a valve or attachment that can be destroyed by a heating pulse.

In a further aspect, the invention also relates to a method for operating such a device. According to this method, all energy storage means e.g. the elastic membranes, are brought into their deformed state, such that all membranes are in their first position where the volume of first the chamber section is large. The first chamber sections are being filled with the target fluid such that they can act as a reservoir, from which the fluid can be released at a later time. The thus prepared device is then operated by individually releasing the energy storage means, e.g. one by one, for conveying defined amounts of target fluid to the channel.

According to a first aspect of the invention, the pump is provided with a plurality of pumping chambers and electrically activatable valves. A deformable membrane is arranged in each pumping chamber and divides the same into a first and a second chamber section. Each valve is connected to the second chamber section of a pumping chamber. When a pressure drop is applied over the valve and the valve is activated (i.e. opened), the pressure in the second chamber section changes, which causes the membrane to move, which in turn leads to a change of the volumes of both chamber sections.

This design allows to convey a target fluid in or out of a chamber section. The energy required for this operation is primarily stored as elastic energy in the membrane (if an elastic membrane is used) and/or is provided by the pressure drop over the valve. The electrical energy required for operating the valve itself can be small, which makes the device attractive for low power applications.

Advantageously, each valve comprises a thermally removable blocking body and a heating means arranged in thermal contact with the blocking body. By operating the heating means, the valve can be activated. This simple design is particularly suited for pumps that are used only once, e.g. in the field of drug delivery. The blocking body is advantageously a material that can be molten or evaporated by the heat from the heating means.

In a second aspect of the invention, the pump is again provided with a plurality of pumping chambers and a membrane dividing the same into a first and a second chamber section. In addition, a plurality of elastic energy storage means is provided, each of which is a) held in a first, elastically deformed state by means of an electrically releasable attachment, and b) releasable from the first position to a second position by releasing the attachment.

By releasing the energy storage means the membrane is moved from the first position to the second position thereby decreasing the volume of the first chamber section and increasing the volume of the second chamber section, which allows to pump a fluid out of the first chamber section or to pump fluid into the second chamber section).

Advantageously, each elastic energy storage means if formed by the membrane itself. Each attachment pulls a corresponding part of the membrane into one of the pumping chambers under elastic deformation. When the attachment is released, the membrane relaxes, thereby moving to decrease the volume of the first chamber section and to increase the volume of the second chamber section.

The pump is suited to convey liquid as well as gaseous fluids. It can have an advantageous ratio between storage volume and total volume.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 1 is a sectional view of an embodiment of the pump,

FIG. 2 is an enlarged sectional view of a single cell of the pump in a first mode of operation prior to activating the valve, FIG. 3 is the view of FIG. 2 after activating the valve, FIG. 4 is an enlarged sectional view of a single cell of the pump in a second mode of operation prior to activating the valve, FIG. 5 is an enlarged sectional view of a single cell of the pump in the second mode of operation after activating the valve, FIG. 6 is a schematic view of a circuit for operating the pump.

DETAILED DESCRIPTION OF THE INVENTION

Figure 7:
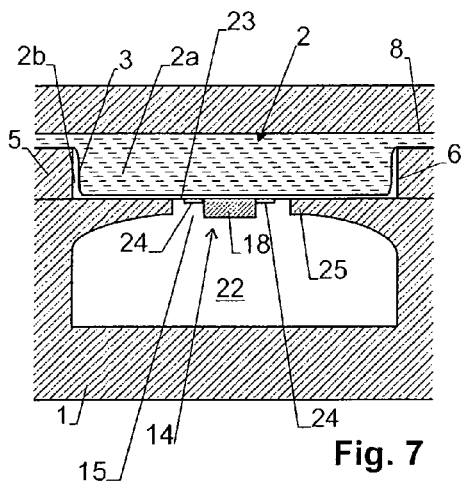
FIG. 7 is an enlarged sectional view of a single cell of a second embodiment of the invention.

Within the context of the present description and claims, the following definitions are used:

The "target fluid" is the fluid to be conveyed, such as a drug in liquid or gaseous form.

The "auxiliary fluid" is a second fluid, which is conveyed to or from the chamber section not used by the target fluid. The auxiliary fluid may be of a material different from the target fluid, but it may also be of the same material.

"Activating" a valve designates the opening of the valve, i.e. the fluid can pass the valve after activation.

First Embodiment

The embodiment of the pump and fluid delivery device shown in FIG. 1 comprises a substrate 1, which is advantageously a plastic substrate, but which may also be of a different material, such as glass or a semiconductor, in particular silicon. On a first side of substrate 1, namely the top side in FIG. 1, there is located a plurality of pumping chambers 2. The pumping chambers 2 can e.g. be arranged in a one-dimensional row or, advantageously, a two-dimensional matrix. Each pumping chamber typically has a volume in the range of a few $\mu m^3$ to several 100000 $\mu m^3$. The device can comprise a large number of pumping chambers, such as 1000 or more.

In the embodiment shown here, the pumping chambers 2 are formed by recesses 6 in substrate 1, which have e.g. been machined by hot-embossing or hot-melt casting techniques as known to the person skilled in the art. Alternatively, the recesses 6 can also be formed by etching techniques.

As can best be seen from FIG. 2, each pumping chamber 2 is divided into two chamber sections 2a, 2b by means of a flexible, elastic membrane 3. Membrane 3 is formed by a flexible, elastic foil 4, which extends through all pumping chambers 2. Membrane 3 is tightly connected, e.g. by gluing or welding, to the top edges of the walls 5 that separate the recesses 2.

The first chamber sections 2a of all pumping chambers 2 are connected to a channel 8 that interconnects all pumping chambers. Channel 8 is formed by a gap between substrate 1 and a cover plate 10, wherein cover plate 10 is located at a distance from the first side of substrate 1. Suitable spacers (not shown), e.g. formed by projections at the top side of substrate 1 or at the bottom side of cover plate 10, can be used to maintain a well-defined gap width. Channel 8 ends in a port section 11, where it can be connected to an external system, such as a tube leading to a needle for drug delivery.

A flow sensor 12 is located at port section 11 of channel 8 and can be used to monitor the amount of conveyed liquid. Flow sensor 12 may e.g. be directly integrated on substrate 1. Suitable types of flow sensors are known to the person skilled in the art and are e.g. described in U.S. Pat. No. 6,550,324.

Also, a flow restrictor 29 may be arranged at port section 11, which is e.g. a narrowed passage and which limits the flow of the pumped liquid to a maximally allowable flow level.

The second chamber sections 2b of all chambers are connected to one of a plurality of electrically activatable valves 14. Each valve serves to close a opening or duct 15 extending from one pumping chamber 2 at the first side of substrate 1 through the substrate 1 to a second, opposite side thereof. In many embodiments, this second side of substrate 1, which is the bottom side in FIG. 1, is one of the outer sides of the device.

A possible design of the valves 14 is e.g. shown in FIG. 2. The valve comprises a blocking body 17 located in opening or duct 15 and closing the same. An electrical heater 18, which acts as a heating means and can e.g. be a resistive heater integrated in substrate 1, is arranged in thermal contact with blocking body 17.

Blocking body 17 is of a material that is solid at the nominal operating temperature of the device, but it can be molten or evaporated by the heat from heater 18 when the heater is activated by an electrical signal. Blocking body 17 can e.g. be of a wax or plastic having a melting temperature in the order of 100° C.

The heaters 18 can be controlled individually by means of suitable driving circuitry, an advantageous embodiment of which is in FIG. 6. The circuitry comprises a power supply 20, an intermediate electrical storage device e.g. in the form of a capacitor C, and a control and switching assembly 21.

For valve activation, control and switching assembly 21 can selectively connect capacitor C to at least one of the valves 14 (i.e. the heaters 18) at a time. The embodiment of FIG. 6 shows an assembly where a single switch is attributed to each valve, which allows to connect each valve to capacitor C. In particular if a large number of pumping chambers 2 is provided in a two dimensional array, matrix switching geometries with row and column driving circuitry can be used as well. Such designs are known to the person skilled in the art.

In the embodiment of FIG. 6, the application of capacitor C as an intermediate electrical storage device provides a fail safe against activation of an exceedingly large number of valves 14 at the same time. In simplified approximation, this is achieved as follows:

Capacitor C has a storage capacity $E=V^2 \cdot C/2$, where V designates the voltage delivered by voltage supply 20, and is able to supply electricity at a first power level P1 limited only by the internal resistance of the capacitor and the resistance of its load.

Power supply 20 is limited to supply electricity at no more than a second power level P2. In the embodiment of FIG.

6, this is illustrated by a resistor R1 in series to the voltage source of power supply 20, which limits the second power level available outside power supply 20 to $P2=V^2/R1/2$.

Each heater 18 of a valve 14 requires a threshold power Pt and threshold energy Et for activation, i.e. for melting the blocking body 17.

By choosing the storage capacity E, the first power level P1 and the second power level P2 such that $$Pt<P1 \text{ and } Pt>P2 \text{ and } Et<E,$$

the maximum power P2 from power supply 20 is not able to directly activate a valve in the presence of a malfunction of the device. In addition, by limiting the energy E that can be stored in capacitor C to $$E<k \cdot Et,$$

with k being a constant larger than 1 but smaller than the maximum number of valves to be activated at the same time plus 1, the energy stored in capacitor C will not allow to activate more than the maximum number of allowable valves at the same time, even in case of a malfunction of control and switching assembly 21. k can e.g. be chosen to be >1 and <2 if the device is to open only a single valve at a time.

Control and switching assembly 21 can be equipped to monitor the heaters 18. This is particularly advantageous when the device is designed such that the heater 18 is destroyed when its valve is activated. In this case, when a valve is activated properly, the corresponding heater 18 will change its impedance (e.g. it will go to a very high value), which can monitored by control and switching assembly 21.

In the following, various applications of the present device are described.

In all these applications, it is assumed that there is a target fluid as defined above, which is the fluid that is to be conveyed by the device, as well as an auxiliary fluid, which is located in the chamber sections not used by the target fluid. Typically, the auxiliary fluid can be air, even though other fluids can be used as well.

Application 1:

In one application, which is particularly advantageous for drug delivery or fuel delivery for fuel cells and similar applications, the target fluid is located in the first chamber sections 2a and needs to be delivered in consecutive, small amounts to channel 8. In other words, the first chamber sections 2a form a reservoir for the fluid to be delivered. Initially, i.e. when the fluid delivery device is in its full, charged state, all membranes 3 are in the first position as shown in FIG. 2 and all (or a large majority of the) first chamber sections 2a are filled with the target fluid. In use, the membranes 3 of the chambers are released, e.g. one at a time, by individually activating the valves 14, e.g. one after the other. Each time a valve 14 is activated, the corresponding membrane 3 moves to its second, relaxed state as shown in FIG. 3, thereby delivering the target fluid from first chamber section 2a to channel 8.

In this application, the pump is prepared by manufacturing substrate 1 and applying the blocking bodies 17 for closing the valves. This can e.g. occur by means of known photolithographic manufacturing techniques, such as microlithographic structuring and etching. Substrate 1 prepared in this way is brought into a vacuum environment. Foil 4 is prepared with a suitable adhesive layer at one side and placed over the top side of substrate 1 with the adhesive layer in contact with the walls 5. The adhesive forms a tight connection with the top edges of these walls. Thermal treatment may be used to improve the quality of the connection.

The assembly of substrate 1 and foil 4 prepared in this way is subjected to ambient pressure, which will cause foil 1 to be pushed into the recesses 6 by elastic deformation. In this state, the volume of the first chamber sections 2a above the membranes 3 will be substantially larger than the volume of the second chamber sections 2b below the membranes 3.

Cover plate 10 can be mounted to substrate 1, either before or after subjecting substrate 1 and foil 4 to ambient pressure.

The target liquid can now be filled into channel 8 and the first chamber sections 2a, e.g. using capillary effects and/or gravity.

In normal operation, the volume V2 at the second (lower) side of substrate 1 must e.g. be brought into connection with air under ambient pressure.

Now, the pump is ready to deliver the target fluid.

To deliver an amount of target fluid, a given number of valves (e.g. a single valve) is activated, which allows auxiliary fluid (air) to enter through the opening(s) or duct (s) 15 into the second chamber section(s) 2b, which in turn allows the membrane(s) 3 of the corresponding pumping chamber(s) 2 to relax, releasing their elastic energy and conveying the target fluid from the first chamber section(s) 2a to channel 8. If the pressure in the target fluid is the same as the one in the auxiliary fluid, the membrane can relax completely, thereby ejecting all target fluid from the first chamber section. If the pressures are not equal, the amount of ejected target fluid depends on the pressures as well as the stiffness of the membrane.

The volume of target fluid ejected through port section 11 of channel 8 can be monitored by means of flow sensor 12.

The ejection procedure can be repeated by successively opening different valves 14, thereby repetitively releasing defined amounts of target fluid to channel 8.

Application 2:

Similarly, the present device can be used for sucking target fluid in through port section 11 of channel 8. In this case, foil 4 is applied to substrate 1 under ambient pressure, thus manufacturing a device where the membranes 3 are in a relaxed state and the first chamber sections 2a have much smaller volumes than the second chamber sections 2b. The second chamber sections 2b are filled by an auxiliary fluid, such as air.

To operate the device, a vacuum is created in volume V2 below substrate 1. To draw in an amount of target liquid, one (or more) of the valves 14 are activated, thereby sucking the auxiliary fluid out of the corresponding second chamber section(s) 2b and deforming the membrane(s) 3, which in turn causes target fluid to be drawn from channel 8 into the first chamber section(s) 2a.

Second Embodiment

FIG. 7 shows a second embodiment of the present invention. In differs from the first embodiment by having a reservoir chamber 22 attributed to each pumping chamber 2. The reservoir chambers 22 replace the common volume V2 of the first embodiment. They serve as an (at least partially) elastic energy storage means and are e.g. filled with a pressurized gas under elevated pressure of e.g. 10 bar, i.e. under a pressure higher than the pressure in pump chamber 2. This filled state corresponds to the "elastically deformed" state of the energy storage means. The pressurized gas is released into second chamber section 2b when valve 14 is activated, thereby pressing fluid from first chamber section 2a into channel 8 and bringing the energy storage means to its relaxed state.

The second embodiment further differs from the first embodiment by the design of valve 14. In the second embodiment, a membrane-like thin film 23 acts as a blocking body and extends through the bottom section of all pump chambers 2, thereby closing the openings or ducts 15. Heaters 18 are arranged on film 23, with at least one heater 18 attributed to each opening or duct 15. When a heater 18 is heated, it locally melts and/or evaporates film 23 thereby forming an opening connecting the corresponding pump chamber 2 to its reservoir chamber 22 and causing the pressurized gas from reservoir chamber 22 to enter into second chamber section 2b.

Advantageously, at least one reservoir chamber 22 is attributed to pump chamber 2 and the reservoir chambers are separate from each other, i.e. they do not communicate. Hence, the pressure available for expanding second chamber section 2b after activating its valve 14 is independent of the number of other valves that have already 14 been opened.

Thin film 23 is, advantageously, of a material having high tensile stiffness such that it is not significantly deformed by the pressure in reservoir chamber 22. To further decrease the deformation of thin film 23, stiff support sections 25 are mounted to the walls 26 that separate the reservoir chamber 22.

Heater 18 is e.g. a resistor connected to metal leads 24 arranged on thin film 23.

Figure 8:
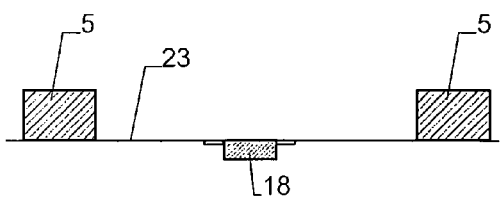
FIG. 8 is a view of the cell of FIG. 7 in a first manufacturing phase.
Figure 9:
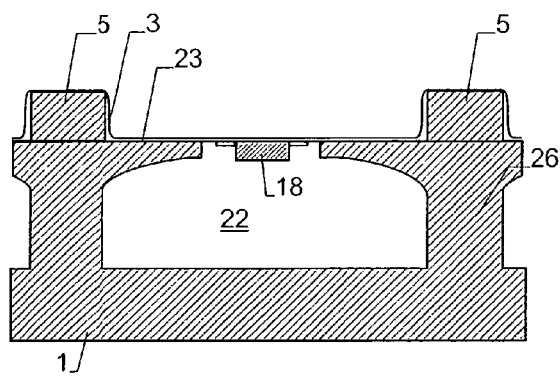
FIG. 9 is a view of the cell of FIG. 7 in a second manufacturing phase.

The pump according to this second embodiment can e.g. be manufactured by the following steps:

a) providing a grid-like matrix of the walls 5 separating the pump chamber 2;

b) applying thin film 23 with the heaters 18 to the bottom side thereof as shown in FIG. 8, c) applying, under elevated pressure, the substrate 1 forming the reservoir cavities 22 to the bottom side of thin film 23;

d) applying, under vacuum conditions, the membrane 3 to the top side of the walls 5 such that it collapses into the chambers 2 under normal pressure, as shown in FIG. 9.

e) Mounting cover plate 10 and filling the pump cavities 2.

Third Embodiment

Figure 10:
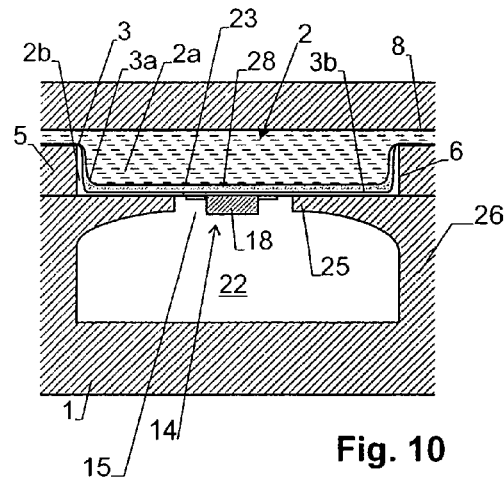
FIG. 10 is an enlarged sectional view of a single cell of a third embodiment of the invention.
Figure 11:
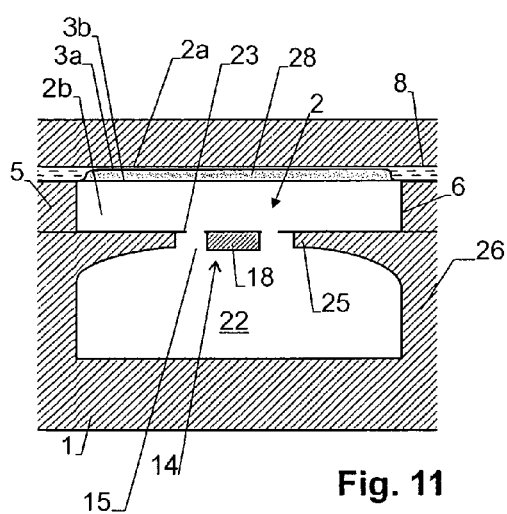
FIG. 11 is the embodiment of FIG. 8 after expansion of the second chamber section.

FIGS. 10 and 11 show a third embodiment of the invention, which is basically similar to the second embodiment but where membrane 3 has increased thickness in the region of pump chamber 2. This can e.g. be achieved if membrane 3 is assembled from a first and a second membrane 3a, 3b, which are interconnected in the regions of the walls 5 and form a blister 28 in each chamber 2. Blister 28 can e.g. be filled by air or by any other suitable fluid.

As shown in FIG. 1, when valve 14 is activated and second chamber section 2b is expanded, the blister 28 extends into channel 8 thereby reducing the amount of residual fluid therein. This is in particular advantageous if, after expansion of chamber section 2b, the pressure in volume V2 or reservoir chamber 22 is not much larger than the one in channel 8.

Alternatively, or in addition to this, the amount of undesired residual fluid in channel 8 can be reduced by reducing the cross section of the channel, e.g. by giving it a width substantially smaller than the width of each pumping chamber 2.

Fourth Embodiment

Figure 12:
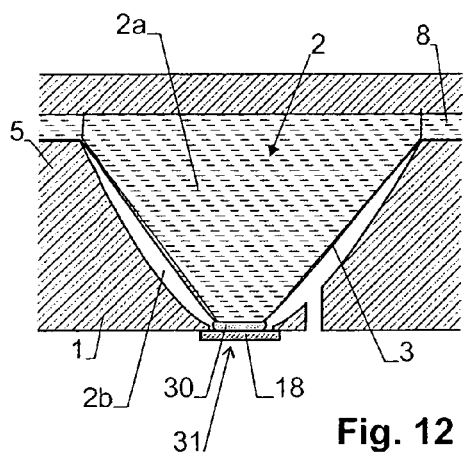
FIG. 12 is an enlarged sectional view of a single cell of a fourth embodiment of the invention.
Figure 13:
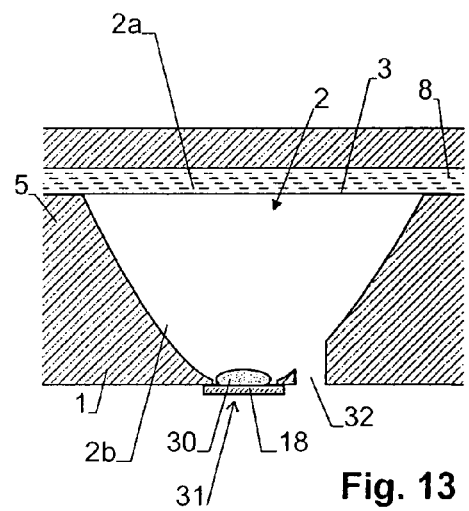
FIG. 13 is the cell of FIG. 12 after expansion of the second chamber section.
Figure 14:
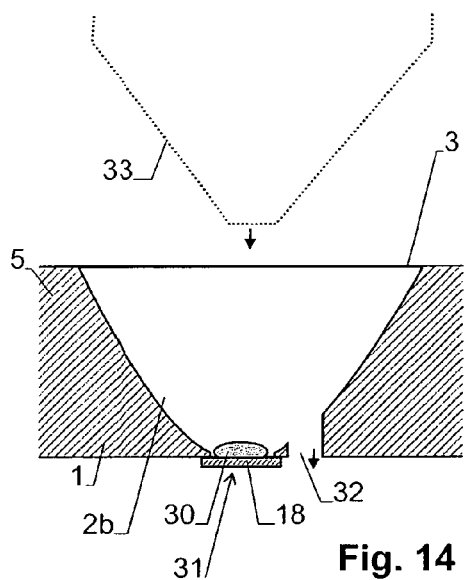
FIG. 14 is the cell of FIG. 12 during manufacturing.

Yet a further embodiment is shown in FIGS. 12 to 14. In this embodiment, pumping chamber 2 is again divided into two chamber sections 2a, 2b by means of flexible membrane 3. In this embodiment, membrane 3 is elastically extendible.

In the "loaded" state of the pump, as shown in FIG. 12, membrane 3 is attached, under elastic extension, to the wall of second chamber section 2b, e.g. by means of a heat releasable glue 30 or by means of welding, in at least one area 31. First chamber section 2a is filled with the fluid to be pumped.

A heater 18 is located in thermal communication with area 31. When it is heated by an electrical signal, the attachment for retaining membrane 3 formed e.g. by glue 30 is destroyed and membrane 3 is released, which allows it to relax to the position shown in FIG. 13.

An opening 32 can be provided from chamber section 2b through substrate 1 for airing second chamber section 2b while membrane 3 is relaxing.

The pump according to this embodiment can e.g. be manufactured by applying membrane 3 to substrate 1 as shown in FIG. 14, whereupon a vacuum is applied to opening 32 for drawing membrane 3 into the recess of chamber 2. At the same time, the glue 30 is heated such that it is in a molten state when membrane 3 comes into contact with it. Then the device is cooled, thereby allowing glue 30 to harden and to form the retaining mechanism of membrane 3 in second chamber section 2b.

The glue 30 can be any suitable material that adheres to membrane 3 and that, under the application of heat, changes its properties such that the adherence to membrane 3 becomes at least so small that membrane 3 is released. Hence, the term "glue" must be understood in a broad manner.

Alternatively, membrane 3 can be pushed into the recess of pump chamber 2 by means of a suitable matrix of stamps, as indicated by reference numeral 33.

In the embodiment of FIGS. 12 to 14, the membrane 3 in each pumping chamber 2 forms an elastic energy storage means, which has two states or positions:

a) In the "loaded" state of the pump or fluid delivery device, the elastic energy storage means is held in an elastically deformed state by means of an electrically releasable retaining mechanism, namely glue 30 and heater 18. In this loaded state, membrane 3 is in a first position. All (or nearly all) first chamber sections are filled with the target fluid to be delivered.

b) For pumping the fluid out of first chamber section 2a, the retaining mechanism or attachment is released by means of an electrical signal to heater 18, thereby releasing the elastic energy storage means. This causes membrane 2 to move into a relaxed state at a second position, thereby decreasing the volume of the first chamber section 2a and increasing the volume of the second chamber section 2b.

The elastic energy storage means may also be a plate spring arranged in the chamber below membrane 3 and attached to the same. In the loaded state of the pump, plate spring is in an elastically deformed, lower position, where it is held by glue 30. When heater 18 is activated and glue 30 melts, thereby releasing the spring, the spring moves upward and pushes membrane 3 into first chamber section 2a.

As can be noted, the embodiment of FIGS. 12 to 14 does not necessarily require a valve, even though it could use a valve. For example, instead of providing a permanently open opening 32, the opening may be formed by heater 18 as in the embodiments above. This allows to combine the technology of the embodiment of FIG. 12 to 14 with those shown in the other figures.

Alternatively, an electrically releasable attachment for retaining the membranes in their deformed state can also be formed by the valves of the embodiments of FIGS. 2 and 3.

In particular, a circuitry of the type shown in FIG. 6 and with the properties described above can be used for heating the heaters 18 that release the glue 30.

Other Applications

In the above applications, the target fluid is conveyed to/from the first chamber sections 2a while the auxiliary fluid is conveyed from/to the second chamber sections 2b.

Alternatively, the target fluid can be conveyed to/from the second chamber sections 2b while the auxiliary fluid is conveyed from/to the first chamber sections 2a. In some applications, this alternative may be less desirable because the target fluid may be contaminated by the presence of material from the blocking bodies 17. To collect and guide the target fluid in this application, volume V2 below substrate 1 can e.g. be formed by a suitable channel, similar to channel 8 at the top side of the embodiment of FIG. 1. Channel 8, on the other hand, may be dispensed with.

From the above it follows that there are basically four methods for operating the device.

1. Upon activating the valves 14, the auxiliary fluid is conveyed to or from the first chamber sections 2a and the target fluid is conveyed from or to the second chamber sections 2b.

2. Upon activating the valves 14, the target fluid is conveyed to or from the first chamber sections 2a and the auxiliary fluid is conveyed from or to the second chamber sections 2b.

3. The pressure drop over the valves 14 is such that, upon activating a valve 14, fluid enters the second chamber section 2b. This can e.g. be achieved by applying foil 4 under vacuum as described above, but it can also be achieved if the pressure in volume V2 is higher than the pressure in the second chamber sections 2b prior to opening the valves.

4. The pressure drop over said the 14 is such that, upon activating a valve 14, fluid exits from the second chamber section 2b. This can e.g. be achieved by artificially decreasing the pressure in the volume V2 as described above, or by elevating the pressure in the chamber sections to a value higher than the pressure in volume V2.

Methods 1 and 2 are alternatives, and methods 3 and 4 are alternatives as well, but method 1 can be combined with either method 3 or 4, and method 2 can also be combined with either method 3 or 4.

As to the embodiment of FIGS. 12-14, the target fluid can either be pumped out of first chamber section 2a or into second chamber section 2b, so the device can be used either for releasing target fluid or for collecting target fluid.

Other Embodiments

The design of the device shown in FIG. 1 can be varied in different ways.

For example, in the embodiment of FIG. 1, a single valve 14 is attributed to each pumping chamber 2. However, e.g. for redundancy purposes or for increasing the speed of fluid exchange, several valves and openings/ducts may be connected to a single pumping chamber 2.

The valves may also be arranged on the second (bottom) side of substrate 1.

The openings or ducts 15 and/or the recesses 6 can also be arranged in cover plate 10, or recesses and/or ducts can be provided in cover plate 10 as well as substrate 1. In particular, channel 8 can be dispensed with if one set of ducts, leading to the first chamber sections, is provided in cover plate 10, and a second set of ducts, leading to the second chamber sections 2b, is provided in substrate 1.

Blocking body 17 may also be formed by a thin membrane extending over opening or duct 15 and comprising a conducting stripe, wherein, for activating the valve, a current sufficiently large for locally melting or evaporating the stripe membrane. In this embodiment, the conducting stripe acts as a heater and blocking body at the same time.

In the embodiments shown so far, the membrane was elastic and it was extended elastically during deformation. However, in the embodiments of FIGS. 1-11 the membrane does not necessarily have to be elastic. It may also form a deformable bellows structure in each pumping chamber 2 that allows deformation to accommodate for the varying pressures in the two chamber sections.

To further increase the safety of the device, several of the valves 14 can be arranged in series in each chamber, which reduces the risk that a valve leak or unintentionally opened valve causes a release of fluid. Similarly, several of the releasable attachments or glue patches 30 of FIGS. 12-14 can be arranged in parallel.

While there are shown and described presently preferred embodiments of the invention, it is to be distinctly understood that the invention is not limited thereto but may be otherwise variously embodied and practised within the scope of the following claims.

The invention claimed is:

1. A multicellular pump comprising
a plurality of pumping chambers,
a deformable membrane arranged in each pumping chamber dividing each pumping chamber into a first and a second chamber section, a channel fluidly connected to said first chamber sections,
a plurality of elastic energy storage means, each of said energy storage means being retained by an electrically releasable retaining mechanism in an elastically deformed state and being releasable by an electric signal to relax from said deformed state to a relaxed state,
wherein releasing said energy storage means moves said membrane from a first position to a second position, thereby decreasing a volume of said first chamber section and increasing a volume of said second chamber section,
wherein said first chamber sections form a reservoir,
wherein each retaining mechanism is formed by an electrically releasable attachment comprising a heater, each of which is attached to one of said elastic energy storage means,
wherein each electrically releasable attachment pulls each deformable membrane into an associated pumping chamber and each deformable membrane is released from the associated pumping chamber by heating said heater, and
wherein each attachment comprises a heat releasable glue.

2. The multicellular pump of claim 1 wherein each elastic energy storage means is formed by said membranes and wherein said deformed state corresponds to said first position and said relaxed state corresponds to said second position.

3. The multicellular pump of claim 1 wherein when all said membranes are in said first position, said first chamber sections are at a full volumetric capacity.

4. The multicellular pump of claim 1 comprising a substrate, wherein said pumping chambers are arranged at a first side of said substrate.

5. The multicellular pump of claim 4 comprising openings or ducts extending from said first side through said substrate to a second side of said substrate opposite said first side, each opening or duct connected to at least one of said pumping chambers.

6. The multicellular pump of claim 4 wherein said substrate comprises a plurality of recesses, wherein said pumping chambers are formed at least in part by said recesses.

7. The multicellular pump of claim 1 wherein said retaining mechanisms are formed by a plurality of electrically activatable valves, each valve being connected to one of said second chamber sections, such that the membrane separating the first chamber section from the second chamber section is movable by activating said valve in a presence of a pressure drop over said valve.

8. The multicellular pump of claim 7 wherein each second chamber section is connected by an opening or duct, which opening or duct is closable by one of said valves, to an outside of said pump.

9. The multicellular pump of claim 7 wherein each valve comprises a thermally removable blocking body and a heating means arranged in thermal contact with said blocking body.

10. The multicellular pump of claim 9 wherein said blocking body is meltable or evaporatable by heating said heating means.

11. The multicellular pump of claim 9 wherein said blocking body is formed by a thin film closing an opening or duct leading to said pump chamber.

12. The multicellular pump of claim 9 wherein the heating means and the blocking body of each pumping chamber are all arranged on a common substrate.

13. The multicellular pump of claim 1 comprising
a flow restrictor for limiting a flow of fluid from or to said pump to a maximally allowable flow value, and/or
a flow sensor for monitoring the flow of the conveyed fluid.

14. A multicellular pump comprising
a plurality of pumping chambers,
a deformable membrane arranged in each pumping chamber dividing each pumping chamber into a first and a second chamber section, a channel fluidly connected to said first chamber sections, wherein said first chamber sections form a reservoir,
a plurality of elastic energy storage means, each of said energy storage means being retained by an electrically releasable retaining mechanism in an elastically deformed state and being releasable by an electric signal to relax from said deformed state to a relaxed state,
wherein releasing said energy storage means moves said membrane from a first position to a second position, thereby decreasing a volume of said first chamber section and increasing a volume of said second chamber section,
an intermediate electrical storage device having an energy storage capacity and being able to supply electricity to a first power level,
a power supply feeding electricity to said intermediate electrical storage device, said power supply being limited to supply electricity at no more than a second power level, and
a control and switching assembly for selectively connecting said intermediate electrical storage device to at least one of said retaining mechanisms at a time,
wherein the retaining mechanism requires a threshold power and threshold energy for activation, wherein said threshold power is below said first power level and above said second power level and said threshold energy is below said energy storage capacity.

15. The multicellular pump of claim 14, wherein the energy storage capacity is smaller than the energy calculated by multiplying the threshold energy and a numerical number which is the maximum number of valves to be activated at the same time plus 1.

16. A multicellular pump comprising
a plurality of chambers,
a deformable membrane arranged in each pumping chamber dividing each pumping chamber into a first and a second chamber section, wherein the deformable membrane isolates a target fluid in said first chamber sections,
a plurality of electrically activatable valves, each valve being connected to the second chamber section, such that the membrane separating the first chamber section from the second chamber section is movable by activating said valve in the presence of a pressure drop over said valve,
a substrate, wherein said pumping chambers are arranged at a first side of said substrate,
openings or ducts extending from said first side through said substrate to a second side of said substrate opposite said first side, each opening or duct connected to at least one of said chambers, wherein at least one of said valves is arranged on said substrate at each opening or duct for closing said opening or duct,
an intermediate electrical storage device having an energy storage capacity and being able to supply electricity at a first power level,
a power supply feeding electricity to said intermediate electrical storage device, said power supply being limited to supply electricity at no more than a second power level, and
a control and switching assembly for selectively connecting said intermediate electrical storage device to at least one of said valves at a time,
wherein at least one of said valves requires a threshold power and threshold energy for activation, wherein said threshold power is below said first power level and above said second power level and said threshold energy is below said energy storage capacity.

17. The multicellular pump of claim 16 wherein each second chamber section is connected by an opening or duct, which is closeable by one of said valves, to an outside of said pump.

18. The multicellular pump of claim 16 wherein each valve comprises a thermally removable blocking body and a heating means arranged in thermal contact with said blocking body.

19. The multicellular pump of claim 18 wherein said blocking body is meltable or evaporatable by heating said heating means and/or wherein said blocking body is formed by a thin film closing an opening or duct leading to said pump chamber.

20. The multicellular pump of claim 18 wherein the heating means and the blocking bodies of said pumping chambers are all arranged on a common substrate.

21. The multicellular pump of claim 16 further comprising a channel connected to said first chamber sections.

22. The multicellular pump of claim 16 wherein the energy storage capacity is smaller than the product of a first value and a second value, wherein the first value is a maximum number of valves to be activated at the same time plus 1, and the second value is the threshold energy.

23. The pump of claim 16 further comprising a plurality of separate reservoir chambers, wherein each pump chamber is connected via at least one valve to at least one reservoir chamber.

24. The multicellular pump of claim 23 wherein each reservoir chamber is attributed to no more than one pump chamber and/or a pressurized gas is arranged in said reservoir chamber.

25. A multicellular pump comprising
a plurality of pumping chambers,
a deformable membrane arranged in each pumping chamber dividing the pumping chamber into a first and a second chamber section,
a plurality of elastic energy storage means, each of said energy storage means being a) held in a first, elastically deformed state by means of an electrically releasable attachment
b) releasable from said first position to a second position by releasing said attachment, wherein releasing said energy storage means moves said membrane from a first position to a second position thereby decreasing a volume of said first chamber section and increasing a volume of said second chamber section, and wherein said first chamber sections from a target fluid reservoir, wherein the reservoir is not in fluid connection with an external reservoir, and wherein said attachment comprises a heater and a heat releasable glue.

26. The multicellular pump of claim 25 wherein each elastic energy storage means is formed by part of said membrane and wherein each attachment pull part of said membrane into one of said pumping chambers under elastic deformation, such that the membrane is movable by releasing said attachment.

27. The multicellular pump of claim 25 comprising
a flow restrictor for limiting a flow or fluid from or to said pump to a maximally allowable flow value and/or
a flow sensor for monitoring the flow of the fluid.

* * * * *